(12) United States Patent
Gerdes et al.

(10) Patent No.: US 7,998,962 B2
(45) Date of Patent: Aug. 16, 2011

(54) ENANTIOMERS OF 2'-FLUORALKY1-6-NITROQUIPAZINE AS SEROTONIN TRANSPORTER POSITRON EMISSION TOMOGRAPHY IMAGING AGENTS AND ANTIDEPRESSANT THERAPEUTICS

(75) Inventors: John M. Gerdes, Coos Bay, OR (US); David B. Bolstad, Stafford Springs, CT (US); Brian R. Kusche, Missoula, MT (US)

(73) Assignee: The University of Montana, Missoula, MT (US)

( * ) Notice: Subject to any disclaimer, the term of this patent is extended or adjusted under 35 U.S.C. 154(b) by 0 days.

(21) Appl. No.: 12/887,782

(22) Filed: Sep. 22, 2010

(65) Prior Publication Data
US 2011/0009419 A1    Jan. 13, 2011

Related U.S. Application Data

(62) Division of application No. 11/796,227, filed on Apr. 26, 2007, now Pat. No. 7,812,162.

(60) Provisional application No. 60/795,602, filed on Apr. 26, 2006.

(51) Int. Cl.
A61K 31/496 (2006.01)
C07D 401/04 (2006.01)

(52) U.S. Cl. .................................. 514/253.06; 544/363

(58) Field of Classification Search ........................ None
See application file for complete search history.

(56) References Cited

OTHER PUBLICATIONS

Lee et al. Bioorganic & Medicinal Chemistry, vol. 15, pp. 3499-3504 (2007).*
Bedurftig S, Wunsch B(2004) Chiral, nonracemic (piperazin-2-yl)methanol derivatives with sigma-receptor affinity. Bioorg Med Chem 12:3299-3311.
Bedurftig S, Wunsch B (2006) Synthesis and receptor binding studies of 3-substituted piperazine derivatives. Eur J Med Chem 41:387-396.
Biegon A. et al. (1993) [I]5-Iodo-6-nitroquipazine: a potent and selective ligand for the 5-hydroxytryptamine uptake complex. II. In vivo studies in rats. Brain Res 619:236-246.
Bishop JE. et al. (1991) Synthesis and in vitro evaluation 2,3-dimethoxy-5-(fluoroalkyl)-substituted benzamides: high affinity ligands CNS dopamine $D_2$ receptors. J Med Chem 34:1612-1624.
Elfving B. et al. (2001) Binding characteristics of selective serotonin reuptake inhibitors with relation to emission tomography studies. Synapse 41:203-211.
Frankle GW. et al. (2004) Comparative evaluation of serotonin transporter radioligands 11C-DASB and 11C-McN 5652 in healthy humans. J Nuc Med 45:682-694.
Gerdes JM. et al. (2000) Serotonin transporter inhibitors: synthesis and binding potency of 2'-methyl- and 3'-methyl-6-notroquipazine. Bioorg Med Chem Lett 10:2643-2646.

Habert E. et al. (1985) Characterization of [3H]paroxetine binding to rat cortical membranes. Eur J Pharmacol 118:107-114.
Henry KL. et al. (2003) Serotonin and cocaine-sensitive inactivation of human serotonin transporters by methanethiosulfonates targeted to transmembrane domain I. J.Biol. Chem. 278:37052-37063.
Henry LK. et al. (2006) Tyr-95 and Ile-172 in transmembrane segments 1 and 3 of the human serotonin transporters interact to establish high affinity recognition of antidepressants. J. Biol. Chem. 281-2012-2023.
Hesse S. et al. (2004) Advances in in vivo imaging of serotonergic neurons in neuropsychiatric disorders. Neurosci Biobehavioral Rev 28:547-563.
Huang Y. et al. (2005) Fluoroinated diaryl sulfides as serotonin transporter ligands: synthesis, structure-activity relationship study, and in vivo evaluation of fluorine-18-Labeled compounds as PET Imaging agents, J Med Chem 48:2559-2570.
Huang Y. et al. (2004) A new positron emission tomography imaging agents for the serotonin transporter: synthesis, pharmacological characterization and kinetic analysis of [$^{11}$c]2-2-(dimethylaminomethyl) phenylthio-S etc. Nuc Med Biol 31:543-556.
Huang Y. et al. (2002) Comparative evaluation in nonhuman promates of five PET radiotracers for imaging the serotonin transporters: McN 5652, ADAM, DASB, DAPA, and.
Hyttel J (1994) Pharmacological characterization of selective serotonin reuptake inhibitors (SSRIs). Int. Clinical Psychopharmacol (9 Suppl) 1:19-26.
Jacobsen EJ. et al. (1999) Piperazine Imadazo[1,5-a]quinoxaline Ureas as High-Affinity GABA Ligands of Dual Functionality. J Med Chem 42:1123.
Jagust WJ. et al. (1993) In vivo imaging of the 5-hydroxytryptamine reuptake site in primate brain using single photon emission computed tomography and [$^{123}$I]5 -iodo-6-nitroquipazine. Eur J Pharmacol 242:189-193.
Jagust WJ. et al. (1995) Iodine-123-5-iodo-6-nitroquipazine: SPECT radiotracer to image the serotonin transporter. J Nuc Med 37:1207-1214.
Karramkam M. et al. (2002) Synthesis of a fluorine-18-labelled derivative of 6-nitroquipazine, as a radioligand for the in vivo serotonin transporter imaging with PET. Bioorg Med Chem 10:2611-2623.
Lee BS. et al. (2003) Synthesis and binding affinities of 6-nitroquipazine analogs for serotonin transporter: Part 3. A potential 5-HT transporter imaging agent, 3-(3-[18 F]fluorpropyl)-6-nitroquipazine. Biorg Med Chem 11:4949-4958.

(Continued)

Primary Examiner — Emily Bernhardt
(74) Attorney, Agent, or Firm — Jean Kyle

(57) ABSTRACT

Racemic mixtures and individual enantiomers of fluorine-18 or carbon-11 radiolabelled 2'-alkyl-6-nitroquipazine ligands are serotonin transporter (SERT) tracers for positron emission tomography (PET) imaging. The non-radioactive ligand forms possess therapeutic antidepressant in vitro and in vivo pharmacological binding profiles in rodent brain and cells expressing human serotonin transporter (hSERT). Twelve 2'-alkyl-6-nitroquipazine ligands potently bind in sub-nanomolar concentrations to the pre-synaptic SERT binding site where established antidepressant drugs bind and inhibit the re-uptake of the neurotransmitter serotonin (5-HT). In vivo tracer studies in rats as well as monkey PET scan trial have demonstrated the fluorine-18 and carbon-11 positron radionuclide labeled tracers perform as quantitative tracers of specific binding the SERT protein in live brain.

15 Claims, 3 Drawing Sheets

OTHER PUBLICATIONS

Lee BS. et al. (1999) A potential 5-HT transporter imaging agent: 3-(3-[18F] fluoropropyl)-6-nitroquipazine. J Label Compd Radiopharm 42(suppl 1):54-56.

Logan J. et al. (1990) Graphical analysis of reversible radioligands binding from time-activity, measurements applied to [N- Cmethyl]-(-)cocaine PET studies in human subjects. J Cereb Blood Flow Metab 10:740-747.

Lundkvist C. et al. (1999) Characterization of bromine-76-labelled 5-bromo-6-nitroquipazine for PET studies of the serotonin transporter Nucl Med Biol 26:501-7.

Mock BH. et al. (1995) Solid-phase reversible trap for [$^{11}$ 11C]carbon dioxide using carbon molecular sieves. Nucl Med Biol 22:667-670.

Naylor A. et al. (1993) A potent new class of k-receptor agonists: 4-substituted 1-(arylacetyl)-2-[(dialkylamino)methyl]piperazines. J Med Chem 36:2075-2083.

Sandell J. et al. (2002) Pet examination of [ C]5-methyl-6-nitroquipazine, a radioligand for visualization of the serotonin transporter. Nuc Med Biol 29:651-656.

Tatsumi M. et al. (1997) Pharmacological profile of andidepressants and related compounds at human monoamine transporters. Eur J Pharmacol 340:249-258.

* cited by examiner

ENANTIOMERS OF 2'-FLUORALKY1-6-NITROQUIPAZINE AS SEROTONIN TRANSPORTER POSITRON EMISSION TOMOGRAPHY IMAGING AGENTS AND ANTIDEPRESSANT THERAPEUTICS

CROSS REFERENCE TO RELATED APPLICATIONS

This application is a divisional of application Ser. No. 11/796,227, filed Apr. 26, 2007 now U.S. Pat. No. 7,812,162; which claims the benefits of U.S. Provisional Application No. 60/795,602, filed Apr. 26, 2006, the disclosure of which is hereby incorporated by reference in its entirety including all figures, tables and drawings.

This invention was made with Government support under Grant No. R15 NS39814-02 awarded by the NIH. The Government has certain rights in the invention.

BACKGROUND OF THE INVENTION

Altered serotonin (5-HT) biogenic amine functions within the central nervous system (CNS) are involved or have been implicated in a number of mental health disorders and clinical therapies. The determination of pre-synaptic serotonin transporter (SERT) populations in discrete cerebral regions of living brain may serve as an indicator of the 5-HT system in health and disease. Regional cerebral SERT density measurements with positron emission tomography (PET) imaging are valuable assessments of 5-HT terminal integrity in living brain. Since SERT densities vary as a function of cerebral region, (e.g., high-midbrain, hypothalamus; modest-limbic system, hippocampus and frontal cortex; and low-cerebellum reference region) and with disease (e.g., within the limbic system and neocortical region, among other regions), clinical PET imaging studies demand reproducible measurements of a range of SERT densities (low to high) across live brain regions. Potent SERT tracers (positron labeled radioligands) with appropriate in vivo profiles (brain penetration, target-to-reference tissue ratios, target tissue specific binding to particular protein, among others) are required. These in vivo tracer performance parameters as a function of evaluating CNS 5-HT integrity with cerebral PET imaging for have recently been discussed [Hesse 2004].

Primate brain SERT PET tracer investigations [Elfving 2001, Frankle 2004, Huang 2004, Huang 2002] have brought forward a refined SERT tracer hypothesis, which contends that candidate imaging tracers suitable for assessing low-high SERT densities are plausible, prospectively when the tracers possess the certain traits, for example: i) high SERT binding affinity, ii) reduced nonspecific (reference region; e.g., cerebellum) binding, and iii) extended kinetic imaging profiles as a function of the enhanced radioligand affinity, compensated for with longer-lived radionuclides (e.g., fluorine-18) that provide extended timeframes for PET scan data collections affording accurate estimates of in vivo SERT densities. A need remains for new and effective image tracers. The identification of tracers possessing the aforementioned in vitro and in vivo qualities solves this problem.

All patents, patent applications, provisional patent applications and publications referred to or cited herein, are incorporated by reference in their entirety to the extent they are not inconsistent with the explicit teachings of the specification.

SUMMARY OF THE INVENTION

The invention encompasses novel [$^{11}$C]2'-alkyloxy- and [$^{18}$F]2'-fluoroalkyl-6-nitroquipazine radioligands, that are candidate PET tracers for efficacious imaging of SERT densities across regions of living primate brain. The discovered [$^{11}$C]alkyloxy- and [$^{18}$F]fluoroalkyquipazine tracers, as either a racemic mixture or enantiomeric pure forms, are with distinct molecular chemical structures and pharmacological potency for the SERT target protein, they possess superior rodent in vivo cerebral penetration and regional cerebral specific binding localizations, potency and other qualities as shown in rat by multiple studies and in monkey, according to a PET imaging study.

DETAILED DESCRIPTION OF THE INVENTION

Figure 1:
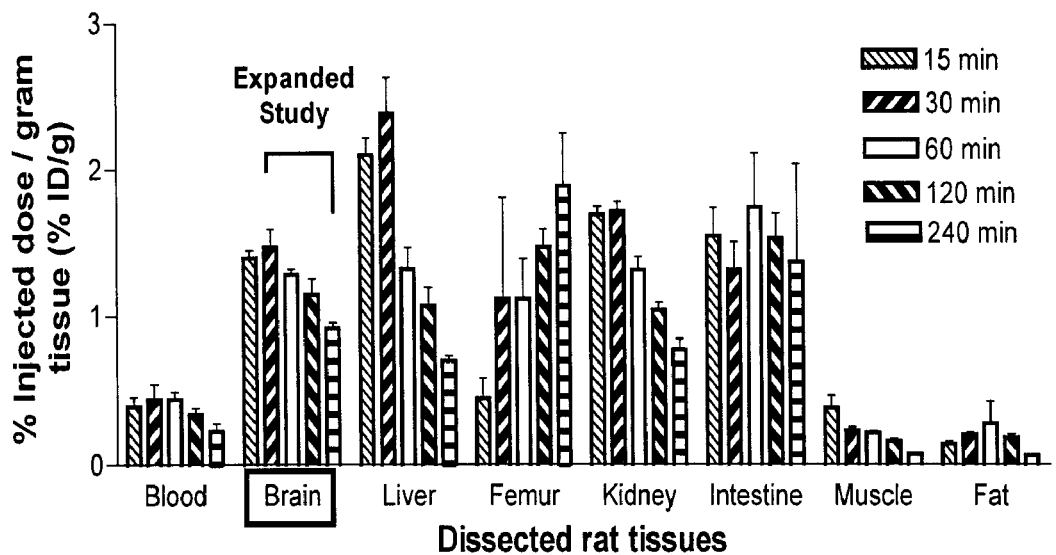
FIG. 1 shows biodistribution (% ID/g)) of tracer [$^{18}$F]]2 in rats (tail vein injection) by organ dissection, and decay corrected radioactivity counting, as a function of time; n=3.

The compounds of the subject invention are serotonin transporter positron emmission tomography imaging agent and antidepressant therapeutics which are enantiomers of 2'-fluoralkyl-6-nitroquipazine. The compounds of the subject invention are described generally in Formula 1.

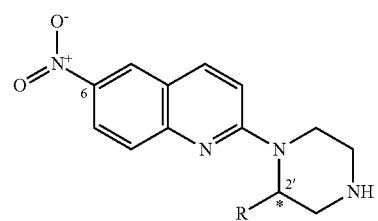

wherein R is selected from the group consisting of $CH_2OCH_3$, $CH_2OH$, $CH_2CH_2CH_2OCH_3$, $CH_2CH_2CH_2OH$, $CH_2CH_2CH_2F$ and $CH_2OCH_2CH_2CH_2F$. All stereoisomers, both enantiomers and diastereomers, and mixtures thereof, are considered to fall within the scope of the subject invention.

TABLE 1

Previously established 6-Nitroquipazine tracers and ligands, with respective SERT competitive binding potency $K_i$ values.

| Cpd | $R_2'$ | $R_3'$ | $R_3$ | $R_5$ | $K_i{}^a$ (nM) | Tracer | Reference |
|---|---|---|---|---|---|---|---|
| 5 | H | H | H | H | 0.16[a,b] | | |
| 6 | H | H | H | I | 0.17[a,c] | [$^{123}$I] | Jagust 1993 & 1995 |
| 7 | H | H | H | Br | 0.13[a,c] | [$^{76}$Br] | Lundkvist 1999 |
| 8 | H | H | H | F | 0.25[a,c] | [$^{18}$F] | Karramkan 2002 |
| 9 | H | H | H | CH$_3$ | — | [$^{11}$C] | Sandell 2002 |
| 10 | H | H | Pr-F | H | 0.31[a,d] | [$^{18}$F] | Lee 1999, Lee 2003 |
| 11 | H | CH$_3$ | H | H | 4.56[a,b] | | |
| 12 | CH$_3$ | H | H | H | 0.08[a,b] | | |

[a]Rat brain, [$^3$H]paroxetine. $K_i$ references:
[b]Ref. Gerdes 2000;
[c]Ref. Mathis 1993.
[d]Rat brain, [$^3$H]citalopram.

A partial summary of the 6-ntiroquipazine molecular framework for the discovery of new SERT PET radioligands within the molecular class as a function of attempts to transform the ligands into useful imaging tracers is found in Table 1, with respective references. For most of the analogs shown, many possess high SERT affinity (Ki<1 nM) and the majority of the analogs are those with changes at position number 5 ($R_5$ in Table 1). None of these established 6-nitroquipazine tracers however serve as useful PET imaging agents. Therefore, from an initial lead compound, ligand 12, a novel analog series has been defined to serve as PET imaging agents (Table 2). The Table 2 ligands have been modified with radiolabelling, which has resulted in the discovery of the racemic and enantiomeric pure forms of the [$^{18}$F]2'-fluoroalkyl-6-nitroquipazine tracers 1 and 2 and [$^{11}$C]2'-alkyloxy-6-nitroquipazine radioligand 13 as novel SERT agents.

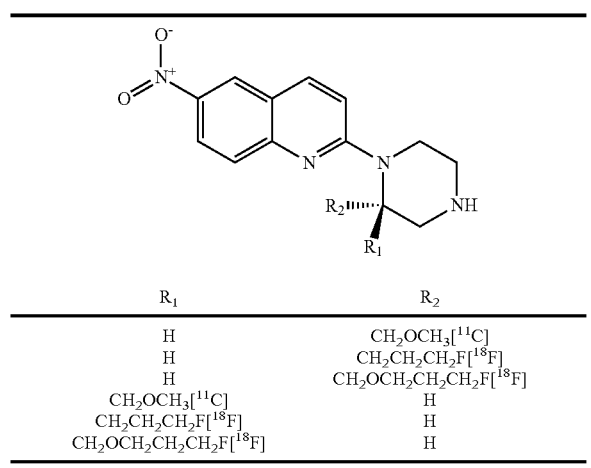

| $R_1$ | $R_2$ |
|---|---|
| H | CH$_2$OCH$_3$[$^{11}$C] |
| H | CH$_2$CH$_2$CH$_2$F[$^{18}$F] |
| H | CH$_2$OCH$_2$CH$_2$CH$_2$F[$^{18}$F] |
| CH$_2$OCH$_3$[$^{11}$C] | H |
| CH$_2$CH$_2$CH$_2$F[$^{18}$F] | H |
| CH$_2$OCH$_2$CH$_2$CH$_2$F[$^{18}$F] | H |

Novel 2'-alkyl-6-nitroquipazines, as described within Table 2 analogs 1-2 and 13-16, in various stereochemical forms have been prepared and possess high SERT binding potency with competitive binding $K_i$ values in sub-nanomolar concentration range. The 2'-alkyl side chain groups as regions for attachment of a fluorine-18 or a carbon-11 radionuclide afford positron emission tomography imaging agents for the serotonin transporter. The carbon-11 and fluorine-18 radiolabelled forms of the analogs are found useful for in vivo imaging of SERT density within discrete cerebral regions. Additionally, the non-radioactive forms of the compounds can be useful as antidepressant therapeutics based on their SERT binding profiles.

TABLE 2

Prepared and characterized 2'-Alkyl-6-nitroquipazine analogs of this invention (ligands 1-2, 13-16) and the known lead agent 12.

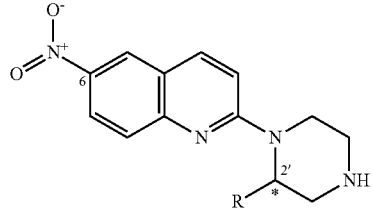

| Cpd | R | Name | Reference |
|---|---|---|---|
| 12 | CH$_3$ (reference) | Me | Gerdes 2000 |
| 13 | (±)-CH$_2$OCH$_3$ | MOM | |
| 13R | (R)—CH$_2$OCH$_3$ | R-MOM | |
| 13S | (S)—CH$_2$OCH$_3$ | S-MOM | |
| 14 | (±)-CH$_2$OH | HOM | |
| 15 | (±)-CH$_2$CH$_2$CH$_2$OCH$_3$ | PrOM | |
| 16 | (±)-CH$_2$CH$_2$CH$_2$OH | PrOH | |
| 1 | (±)-CH$_2$CH$_2$CH$_2$F | PrOF | |
| 1R | (R)—CH$_2$CH$_2$CH$_2$F | R-PrOF | |
| 1S | (S)—CH$_2$CH$_2$CH$_2$F | S-PrOF | |
| 2 | (±)-CH$_2$OCH$_2$CH$_2$CH$_2$F | MePrOF | |
| 2R | (R)—CH$_2$OCH$_2$CH$_2$CH$_2$F | R-MePrOF | |
| 2S | (S)—CH$_2$OCH$_2$CH$_2$CH$_2$F | S-MePrOF | |

[a]The symbol * indicates a stereochemical center, where (±) is the racemic form, (R) is the R-configurational enantiomer and (S) is the S-configurational enantiomer.

The ligands of Table 2 were prepared according to the synthetic routes delineated in Schemes 1-3. The route exemplified in Scheme 1 is general, where a variety of starting material amino acids, similar to that shown as (S)-17, can be employed for the production of the Table 2 ligands. The starting material (S)-17 and similar starting material reagents are prepared by established procedures [Bedurftig 2004, Bedurftig 2006, Naylor 1993].

Scheme 1. Example preparation of ligand 13S is shown below.

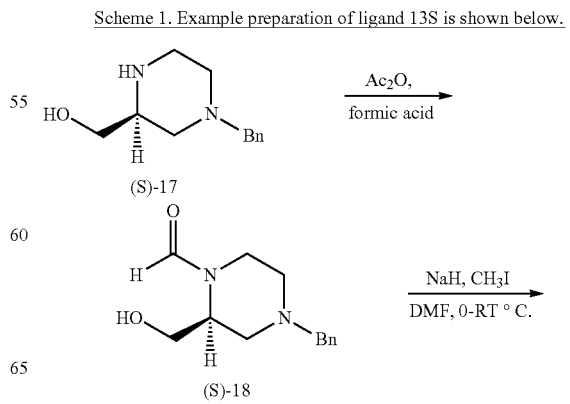

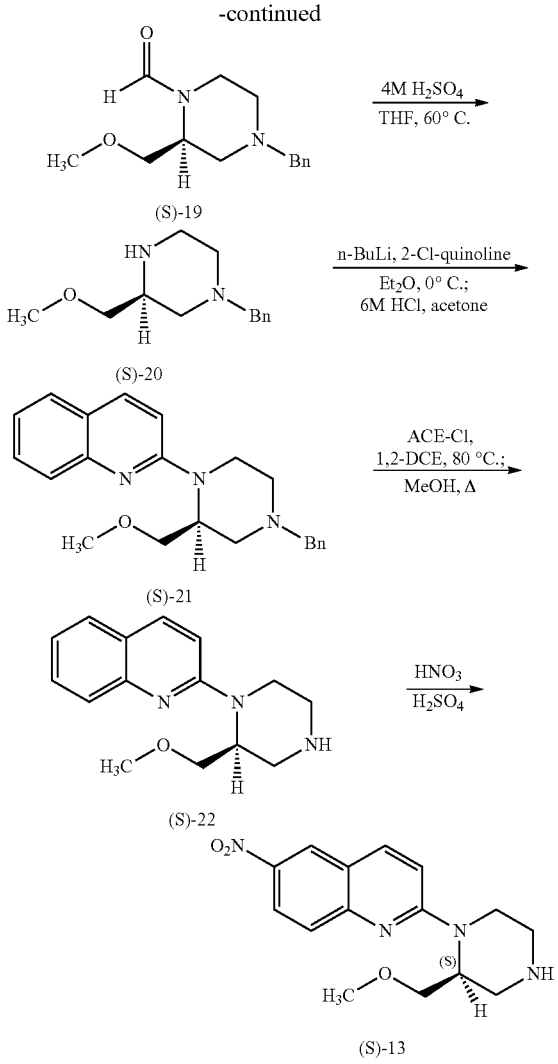

To a 0° C. solution of alcohol (S)-17 (0.567 g, 2.75 mmol) in formic acid (88%, 8 mL) was added (drop-wise) acetic anhydride (2.33 mL, 24.7 mmol). The reaction was stirred for 30 min at 0° C. then warmed to ambient temperature. Following 1 h the reaction was diluted with ice and made basic with 4 N NaOH. The aqueous mixture was further diluted with saturated NaHCO$_3$ and extracted with CH$_2$Cl$_2$. The combined extracts were dried (K$_2$CO$_3$) and concentrated to give an orange-brown oil that was purified by column chromatography to afford (S)-(−)-4-Benzyl-2-(hydroxymethyl)piperazine-1-carbaldehyde, (S)-18 as a colorless oil (0.521 g, 67%). $^1$H NMR (400 MHz, CDCl$_3$): δ 2.05 (td, J=3.7, 11.7 Hz, 0.5H), 2.13 (td, J=3.7, 11.7 Hz, 0.5H), 2.28 (dd, J=4.0, 11.7 Hz, 1H), 2.87 (m, 1H), 2.90-3.02 (m, 1H), 3.12 (td, J=4.0, 12.8 Hz, 0.5H), 3.41-3.59 (m, 3.5H), 3.64-3.75 (m, 1H), 3.85 (m, 0.5H,), 3.97 (dd, J=5.5, 11.4 Hz, 0.5H), 4.08 (dd, J=7.3, 11.4 Hz, 0.5H), 4.20 (bd, 0.5H), 4.38 (m, 0.5H), 7.25-7.36 (m, 5H), 8.06 (s, 0.5H), 8.08 (s, 0.5H).

To a 0° C. solution of alcohol (S)-18 (0.502 g, 2.14 mmol) in dry DMF (20 mL) was added NaH (95%, 0.154 g, 6.43 mmol) in one portion. After stirring 5 min, iodomethane (0.319 g, 2.25 mmol) was added (drop-wise) and the mixture stirred for 20 min at 0° C. then at ambient temp for 1.5 h. The excess NaH was destroyed by the careful addition of water and the solution was diluted with 40 mL each of water and saturated NaHCO$_3$. The aqueous mixture was extracted with ether and ethyl acetate. The combined extracts were washed with brine, then dried (K$_2$CO$_3$) and concentrated to give a brown oil that was purified by column chromatography to afford (S)-(−)-4-Benzyl-2-(methoxymethyl)piperazine-1-carbaldehyde, (S)-19 as an almost colorless oil (0.360 g, 69%). $^1$H NMR (400 MHz, CDCl$_3$): δ 2.00-2.12 (m, 1.3H), 2.18 (dd, J=3.7, 11.7 Hz, 0.7H), 2.80-2.92 (m, 2H), 2.93-3.02 (m, 1H), 3.29-3.38 (m, 3H), 3.41-3.76 (m, 5H), 4.16 (bd, 0.7H), 4.60 (m, 0.3H), 7.25-7.35 (m, 5H, overlapped with CDCl$_3$), 8.04 (s, 0.7H), 8.07 (s, 0.3H).

A solution of (S)-20 (0.320 g, 1.29 mmol) in THF (3 mL) and 4 M H$_2$SO$_4$ (9 mL) was heated at 55° C. for 5 h. After cooling, the reaction contents were poured into 20 mL of cold (−10° C.) 4 M NaOH and diluted with 20 mL of saturated NaHCO$_3$. The mixture was extracted with CH$_2$Cl$_2$ and the combined extracts dried (K$_2$CO$_3$) and concentrated to provide (S)-(+)-1-Benzyl-3-(methoxymethyl)piperazine, (S)-20 as a pale oily solid (0.274 g, 96%). This product was of adequate purity for the subsequent transformations. $^1$H NMR (400 MHz, CDCl$_3$): δ 1.85 (t, J=10.3 Hz, 1H), 2.11 (td, J=3.3, 11.0 Hz, 1H), 2.35 (bs, 1H, NH), 2.74 (m, 2H), 2.90 (m, 1H, td shape), 2.96-3.06 (m, 2H), 3.25-3.36 (m, 5H, OCH$_3$ singlet present at 3.33), 3.50 (m, AB pattern, J=13.2 Hz, 2H), 7.22-7.33 (m, 5H, overlapped with CDCl$_3$).

To a 0° C. solution of (S)-20 (0.273 g, 1.24 mmol) in dry ether (16 mL) under argon was added (dropwise) a solution of n-butyllithium in hexane (2.45 M, 1.24 mmol) producing a clear yellow solution. After stirring 20 min a solution of 2-chloroquinoline (0.134 g, 0.821 mmol) in ether (3 mL) was added (dropwise) and the solution allowed to stir for 10 min at 0° C. then at ambient temperature for 16 h. The reaction contents were diluted with ether, washed with saturated NaHCO$_3$ and brine, then dried (K$_2$CO$_3$) and concentrated to give the crude material that was purified by column chromatography to provide (S)-(−)-2-[4-Benzyl-2-(methoxymethyl)piperazin-1-yl]quinoline, (S)-21 as a thick, light yellow oil (0.275 g, 96%). $^1$H NMR (400 MHz, CDCl$_3$): δ 2.17-2.27 (m, 2H), 2.95 (bd, J=10.3 Hz, 1H), 3.11 (bd, J=11.7 Hz, 1H), 3.21 (m, 1H), 3.33 (s, 3H), 3.49-3.63 (m, 3H), 3.87 (m, 1H), 4.45 (bd, 1H), 4.57 (bs, 1H), 6.98 (d, J=9.2 Hz, 1H), 7.21 (m, 1H), 7.27 (m, 1H, overlapped with CDCl$_3$), 7.31-7.39 (m, 4H), 7.52 (m, 1H), 7.59 (d, J=8.1 Hz, 1H), 7.68 (d, J=8.4 Hz, 1H), 7.87 (d, J=9.2 Hz).

To a 0° C. solution of methyl ether (S)-21 (0.119 g, 0.34 mmol) in dry dichloroethane (8 mL) under argon was added 1-chloroethyl chloroformate (0.093 g, 0.65 mmol). After stirring at 0° C. for 10 min the flask was heated at reflux for 2.5 h. The solution was cooled slightly and the volatile components were evaporated. The residue was dissolved in methanol (10 mL), heated at 60-70° C. for 1 h, and then the solvent was evaporated. The residue was dissolved in 15 mL 1 M HCl and washed with CH$_2$Cl$_2$. The aqueous phase was made basic with 4 M NaOH, diluted with saturated NaHCO$_3$ and extracted with CH$_2$Cl$_2$. The combined extracts were dried (K$_2$CO$_3$) and concentrated to give (S)-(−)-2-[2-(Methoxymethyl)piperazin-1-yl]quinoline, (S)-22 as a pale colored oil (0.081 g, 92%). $^1$H NMR (400 MHz, CDCl$_3$): δ 1.93 (bs, NH, 1H), 2.87 (m, 1H), 2.98 (dd, J=4.0 Hz and 12.5 Hz, 1H), 3.11-3.20 (m, 2H), 3.29-3.37 (m, 4H, overlapped singlet at 3.36, OCH$_3$), 3.48 (dd, J=4.8 and 9.2 Hz, 1H), 3.86 (m, 1H), 4.36 (bd, 1H), 4.57 (bm, 1H), 6.97 (d, J=9.2 Hz, 1H), 7.21 (m, 1H), 7.52 (m, 1H), 7.59 (m, 1H), 7.68 (d, J=8.8 Hz, 1H), 7.88 (d, J=9.2 Hz, 1H).

To a 0° C. solution of (S)-22 (0.038 g, 0.15 mmol) in conc. H$_2$SO$_4$ (2 mL) was added HNO$_3$ (15.4 M, 0.038 mL, 0.59 mmol). The reaction was stirred 17 min then quenched by transfer onto ice. The solution was basified with 4 M NaOH then diluted with saturated NaHCO₃ (10 mL). The bright yellow aqueous mixture was extracted with CH₂Cl₂ and the combined extracts dried (K₂CO₃) and concentrated to provide (S)-(−)-2-[2-(Methoxymethyl)piperazin-1-yl]-6-nitroquinoline, (S)-13 as a bright yellow-orange oily solid (0.040 g, 91%). ¹H NMR (400 MHz, CDCl₃): δ 1.77 (bs, 1H), 2.87 (td, J=3.3, 11.7 Hz, 1H), 2.98 (dd, J=4.4, 12.5 Hz, 1H), 3.15-3.28 (m, 2H), 3.32 (m, 1H), 3.37 (s, 3H), 3.60 (dd, J=5.5, 9.2, 1H), 3.85 (dd, J=7.7, 9.2 Hz, 1H), 4.50 (bm, 1H), 4.66 (bm, 1H), 7.08 (d, J=9.2 Hz, 1H), 7.65 (d, J=9.2 Hz, 1H), 7.96 (d, J=9.2 Hz, 1H), 8.29 (dd, J=2.6, 9.2 Hz, 1H), 8.54 (d, J=2.6 Hz, 1H); ¹³C NMR (100 MHz, CDCl₃): δ 45.9, 46.3, 50.9, 59.1, 70.2, 110.9, 121.0, 123.5, 124.2, 127.0, 138.5, 141.7, 151.4, 158.5; HRMS (ESI-TOF) m/z (M+H)⁺ calcd. for C₁₅H₁₉N₄O₃ 303.1457 found 303.1448; [α]$_D^{25}$ −137.8 (c 0.0023, CHCl₃).

In another example, the ligand 2 can be prepared according to the route of Scheme 2, employing the starting material 13. The Scheme 2 route affords either racemic or enantiomerically pure forms of the ligands depending upon the stereochemistry of the starting material 13.

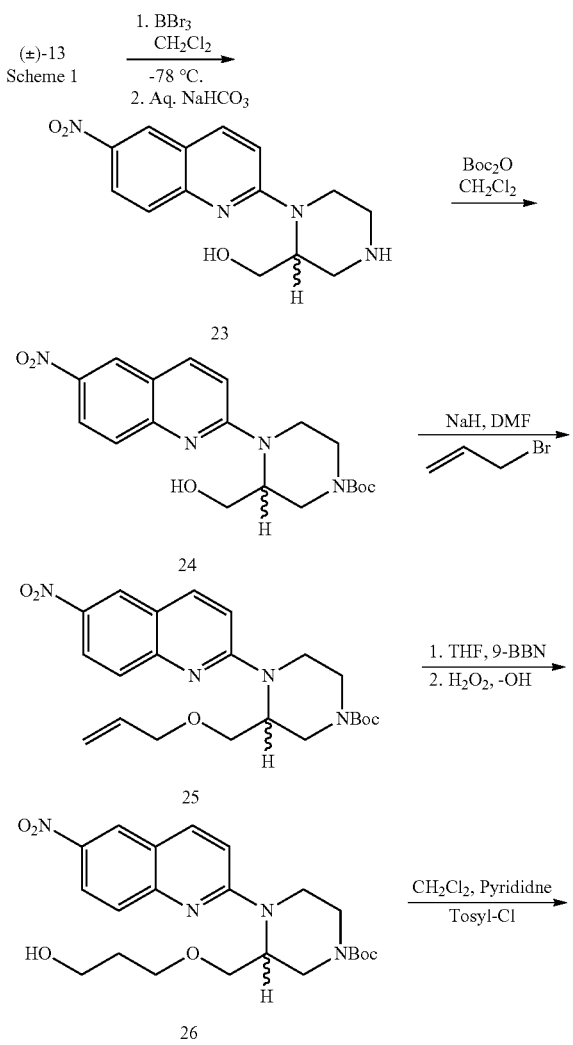

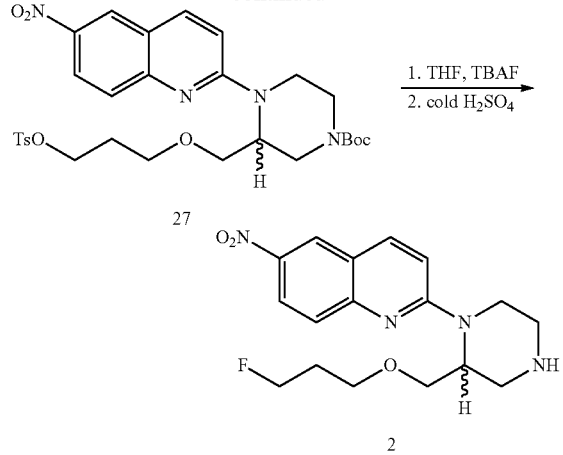

To a −78° C. stirring solution of 13 (0.143 g, 0.474 mmol) in dry CH₂Cl₂ (75 mL) under argon was added (drop-wise) borontribromide solution (1 M in CH₂Cl₂, 2.37 mL, 2.37 mmol). The reaction was maintained at −78° C. for 3 h then warmed to ambient temperature and stirred 18 h. The reaction was quenched with saturated NaHCO₃, transferred to a separation funnel and shaken. The organic phase was separated and the aqueous layer extracted with CH₂Cl₂ and CHCl₃ with isopropyl alcohol. The combined organic phases were dried (K₂CO₃), and concentrated to give a crude residue. The crude residue was dissolved in about 20 mL of CH₂Cl₂ and to this was added a solution of di-tert-butyldicarbonate (0.124 g, 0.569 mmol) in CH₂Cl₂ (5 mL). The solution was stirred for 5 min, concentrated and the residue purified by column chromatography to afford 2-[4-(tert-Butoxycarbonyl)-2-(hydroxymethyl)piperazin-1-yl]-6-nitro-quinoline, 24 as a bright yellow foam (0.129 g, 70%). ¹H NMR (400 MHz, CDCl₃): δ 1.47 (s, 9H), 3.09-3.62 (bm, 4H), 3.66-3.96 (bm, 2H), 3.98-4.43 (bm, 3H), 4.82 (bm, 1H), 7.07 (d, J=9.2 Hz, 1H), 7.61 (d, J=9.2 Hz, 1H), 7.97 (d, J=9.2 Hz, 1H), 8.25 (dd, J=2.6, 9.2 Hz, 1H), 8.47 (d, J=2.6 Hz, 1H).

To a 0° C. solution of 24 (0.194 g, 0.50 mmol) in dry DMF (8 mL) under argon was added NaH (95%, 0.046 g, 1.92 mmol) in one portion. Allyl bromide (0.302 g, 2.5 mmol) was added (drop-wise) to the mixture and the reaction warmed to ambient temperature. After stirring 1.5 h the reaction mixture was carefully added to a separatory funnel containing ether (30 mL) and 16 mL each of water and saturated NaHCO₃. The aqueous phase was separated and the organic phase was washed with brine, dried (K₂CO₃) and concentrated to provide the crude material that was purified by column chromatography to afford 2-[4-(tert-Butoxycarbonyl)-2-(allyloxymethyl)piperazine-1-yl]-6-nitroquinoline, 25 as a bright yellow foam (0.192 g, 90%). ¹H NMR (400 MHz, CDCl₃): δ 1.49 (s, 9H), 2.96-3.37 (bm, 3H), 3.49-3.68 (m, 2H), 3.93-4.78 (bm, 6H), 5.04-5.31 (bm, 2H), 5.82 (bm, 1H), 7.08 (d, J=9.2 Hz, 1H), 7.63 (d, J=9.2 Hz, 1H), 7.95 (d, J=9.2 Hz, 1H), 8.25 (dd, J=2.6, 9.2 Hz, 1H), 8.49 (d, J=2.6 Hz, 1H).

To 25 (0.075 g, 0.175 mmol) in dry THF (600 μL) under argon was added a solution of 9-BBN in THF (0.5 M, 950 μL, 0.475 mmol). The reaction was heated to 55° C. and maintained for 1 h. After cooling to 0° C. 0.6 mL of 1 M NaOH was added (drop-wise) followed by 0.6 mL of 30% H₂O₂. The mixture was stirred for 5 min. The mixture was poured into 20 mL of saturated NaHCO₃ and the aqueous phase extracted with CH₂Cl₂. The combined extracts were dried (K₂CO₃) and concentrated to give the crude material that was purified by column chromatography to afford 2-[4-(tert-Butoxycarbonyl)-2-((3-hydroxypropoxy)methyl)-piperazine-1-yl]-6-nitroquinoline, 26 as a bright yellow foam (0.057 g, 73%). $^1$H NMR (400 MHz, CDCl$_3$): δ 1.49 (s, 9H), 1.73 (bm, 2H), 2.98-3.37 (bm, 3H), 3.41-3.89 (bm, 7H), 4.02-4.53 (bm, 3H), 4.71 (bm, 1H), 7.06 (d, J=9.2 Hz, 1H), 7.64 (d, J=9.2 Hz, 1H), 7.96 (d, J=9.2 Hz, 1H), 8.25 (dd, J=2.6, 9.2 Hz, 1H), 8.49 (d, J=2.6 Hz, 1H).

To a 0° C. solution of alcohol 26 (0.095 g, 0.213 mmol) in dry CH$_2$Cl$_2$ (1.2 mL) and pyridine (100 μL) was added p-toluenesulfonyl chloride (0.170 g, 0.895 mmol) in one portion. The reaction was sealed under argon and maintained in an ice bath until the bath warmed to ambient temperature. After 24 h the reaction contents were partitioned between saturated NaHCO$_3$ (20 mL) and CH$_2$Cl$_2$ (10 mL). The organic phase was separated and the aqueous phase was extracted with CH$_2$Cl$_2$. The combined extracts were dried (K$_2$CO$_3$) and concentrated to give the crude material that was purified by column chromatography to afford 2-[4-(tert-Butoxycarbonyl)-2-((3-(4-methylbenzenesulfonate)propoxy)methyl)piperazine-1-yl]-6-nitroquinoline, 27 as a bright yellow foam (0.103 g, 80%). $^1$H NMR (400 MHz, CDCl$_3$): δ 1.48 (s, 9H), 1.79 (bm, 2H), 2.42 (s, 3H), 2.94-3.30 (bm, 3H), 3.44-3.60 (bm, 4H), 4.02 (bm, 2H), 4.10-4.24 (m, 2H), 4.50 (bm, 1H), 4.65 (bm, 1H), 7.07 (d, J=9.2 Hz, 1H), 7.30 (d, J=8.1 Hz, 2H), 7.63 (d, J=9.2 Hz, 1H), 7.72 (d, J=8.1 Hz, 2H), 7.95 (d, J=9.2 Hz, 1H), 8.26 (dd, J=2.6, 9.2 Hz, 1H), 8.50 (d, J=2.6 Hz, 1H).

To a solution of 27 (0.0238 g, 0.040 mmol) in dry THF (400 μL) was added a solution of TBAF in THF (1 M, 0.06 mL, 0.06 mmol). The reaction was sealed under argon and heated at 55-60° C. for 3 h. After cooling, the THF was evaporated and the residue was purified by column chromatography to afford the N-Boc protected intermediate as a yellow film (0.0137 g, 77%). To this intermediate (0.0217 g, 0.048 mmol) in a flask at 0° C. was added cold (−10° C.) conc. H$_2$SO$_4$ (3 mL) and the flask was swirled to clear the sides of material. After 5 min the contents were transferred onto ice, made basic with 4 M NaOH and further diluted with saturated NaHCO$_3$. The yellow aqueous mixture was extracted with CH$_2$Cl$_2$ and the combined extracts were dried (K$_2$CO$_3$) and concentrated to give the crude material that was purified by column chromatography to afford 2-[2-((3-Fluoropropoxy)methyl)piperazine-1-yl]-6-nitroquinoline, 2 as a yellow film (0.013 g, 80%). $^1$H NMR (400 MHz, CDCl$_3$): δ 1.80-2.00 (m, 3H, overlapped bs of NH and dp, $J_{F-H}$=26.0 Hz, FCH$_2$CH$_2$—, $J_{H-H}$=6.2 Hz), 2.87 (m, 1H), 2.99 (m, 1H), 3.12-3.36 (m, 3H), 3.58 (t, J=6.2 Hz, 2H), 3.68 (dd, J=5.5, 9.5 Hz, 1H), 3.88 (dd, J=7.3, 9.5 Hz, 1H), 4.44 (dt, $J_{F-H}$=47.2, FCH$_2$—, $J_{H-H}$=5.9 Hz, 2H, overlapped with a bs at 4.50, 1H), 4.66 (bs, 1H), 7.08 (d, J=9.2 Hz, 1H), 7.63 (d, J=9.2, 1H), 7.95 (d, J=9.2, 1H), 8.28 (dd, J=2.6, 9.2 Hz, 1H), 8.52 (d, J=2.6, 1H); $^{13}$C NMR (100 mHz, CDCl$_3$): δ 30.7 ($J_{C-F}$=19.8 Hz, FCH$_2$CH$_2$—), 41.3, 45.9, 46.4, 50.0, 67.0 ($J_{C-F}$=6.1 Hz, FCH$_2$CH$_2$CH$_2$—), 68.5, 81.0 ($J_{C-F}$=164.8 Hz, FCH$_2$—), 111.1, 121.1, 123.6, 124.2, 127.1, 138.4, 141.8, 151.4, 158.7; HRMS (ESI-TOF) m/z (M+H)$^+$ calcd. for C$_{17}$H$_{22}$N$_4$O$_3$F 349.1676 found 349.1674.

In another example, the ligand 1 may be prepared according to the route of Scheme 3, employing the ligand 15 as starting material. A synthetic route similar to that described in Scheme 1 affords the requisite starting material 15.

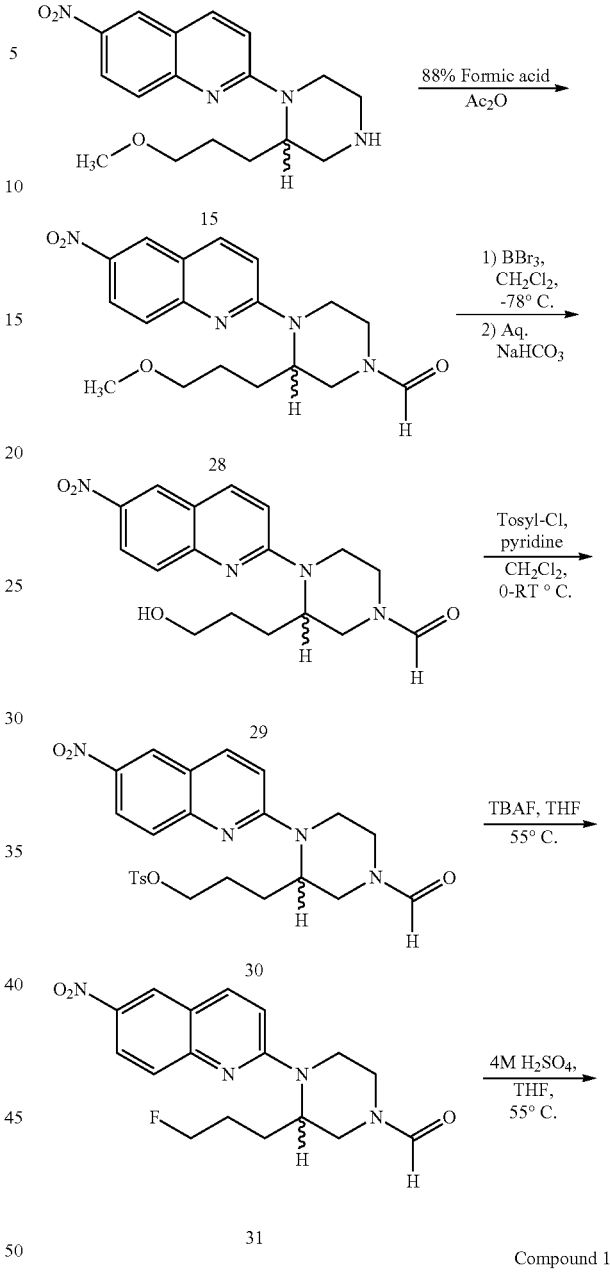

Scheme 3. Preparation of ligand 1.

A solution of 15 (0.19 g, 0.58 mmol) in 88% formic acid (1.5 mL) was treated with acetic anhydride (Ac$_2$O) (0.54 g, 0.5 mL, 5.2 mmol) and the reaction stirred for 30 min. The reaction was quenched by pouring onto ice, then brought to basic pH with 4 M NaOH, buffered to pH 10 with sat. NaHCO$_3$. The basic portion was extracted with CH$_2$Cl$_2$. The organic portions were combined, dried (K$_2$CO$_3$), and concentrated in vacuo to give N-Formyl-3-(3-methoxypropyl)-4-(6-nitroquinolin-2-yl)piperazine, 28 as a yellow oil (0.19 g, 91%). NMR (CDCl$_3$, 400 MHz) δ 1.45-1.90 (m, 4H), 2.9 (dt, J=4.2 and 12.6 Hz, 0.5H), 2.98 (dd, J=3.9 and 13.3, 0.5H), 3.14-3.43 (m, 7.5H), 3.44-3.51 (m, 0.5H), 3.58 (bd, 0.5H), 3.70 (bd, 0.5H), 4.45 (bt, 1H), 4.74 (bs, 0.5H), 4.91 (bs, 0.5H), 7.70 (dd, J=7.4 and 9.1 Hz, 1H), 7.63 (d, J=9.1 Hz, 1H), 7.98 (d, J=9.4 Hz, 1H), 8.09 (s, 0.5H), 8.2 (s, 0.5H), 8.28 (dd, J=2.6 and 9.1 Hz, 1H), 8.51 (d, J=2.6 Hz, 1H).

A solution of 28 (0.19 g, 0.53 mmol) in dry $CH_2Cl_2$ (25 mL) was cooled at −78° C. in a dry ice acetone bath. A solution of $BBr_3$ (2.6 mL, 1 M in $CH_2Cl_2$, 2.6 mmol, Aldrich) was added drop-wise under argon and stirred for 2 h, and then the reaction was warmed to RT ° C. and stirred for 2.5 h. The reaction was quenched by the addition of sat. $NaHCO_3$ (20 mL), the organic portion was separated and the aqueous was extracted with $CH_2Cl_2$. The organic portions were combined, dried ($K_2CO_3$), filtered and concentrated in vacuo and the resultant crude material was purified by column chromatography to afford N-Formyl-3-(3-hydroxypropyl)-4-(6-nitroquinolin-2-yl)piperazine, 29. $^1H$ NMR ($CDCl_3$, 400 MHz) δ 1.48-1.96 (m, 5H), 2.88-3.08 (m, 1H), 3.24-3.45 (m, 1.5H), 3.50 (dd, J=3.9 and 13.6 Hz, 0.5H), 3.61 (bd, J=13.3 Hz, 0.5H), 3.66-3.84 (m, 2.5H), 4.24-5.15 (bm, 3H), 7.11 (d, J=9.4 Hz, 1H), 7.76 (bs, 1H), 8.04 (d, J=9.1 Hz, 1H), 8.12 (s, 0.5H), 8.26 (s, 0.5H), 8.33 (dd, J=2.6 and 9.4 Hz, 1H), 8.57 (d, J=2.6 Hz, 1H).

A solution of 29 (0.081 g, 0.24 mmol) in dry $CH_2Cl_2$ (0.5 mL) and dry pyridine (0.029 g, 0.37 mmol) was cooled at 0° C. To the solution was added tosyl chloride (0.062 g, 0.33 mmol). The solution was allowed to stir at 25° C. for 3 h. The crude reaction mixture was purified by column chromatography to give 3-(4-Formyl-1-(6-nitroquinolin-2-yl)piperazin-2-yl)propyl-4-methylben-zenesulfonate, 30 as a yellow foam (0.060 g, 51% yield). $^1H$ NMR ($CDCl_3$, 400 MHz) δ 1.70-2.02 (m, 8H), 2.44 (s, $ArCH_3$, 3H), 2.90 (dt, J=4.2 and 12.6, 1H), 3.03 (dd, J=3.9 and 13.3 Hz), 3.20-3.60 (m, 10H), 3.73 (bd, 1H), 4.30-4.70 (4 m, 4H), 4.88 (bs, 1H), 5.10 (bs, 1H), 7.07 (dd, J=2.9 and 9.1 Hz, 2H), 7.33 (d, J=7.8 Hz, 2H), 7.66 (dd, J=4.5 and 9.4 Hz, 2H), 7.78 (d, J=8.1 Hz, 2H), 8.03 (d, J=9.4 Hz, 2H), 8.12 (s, 2H), 8.26 (s, 1H), 8.31 (dd, J=2.6 and 9.4 Hz, 2H), 8.55 (d, J=2.6 Hz, 2H).

A solution of 3-(4-formyl-1-(6-nitroquinolin-2-yl)piperazin-2-yl)propyl4-methylbenzene-sulfonate 30 (0.056 g, 0.11 mmol) in dry THF (0.30 mL) was treated with a solution of TBAF (0.16 mL, 1 M in THF, 0.16 mmol) to give a dark orange solution. The reaction mixture was heated at 55° C. for 2 h, and then was concentrated in vacuo and diluted with $CHCl_3$. The crude material was purified by column chromatography to give N-Formyl-3-(3-fluoropropyl)-4-(6-nitroquinolin-2-yl)piperazine, 31 as a yellow foam (0.025 g, 64%). $^1H$ NMR ($CDCl_3$, 400 MHz) δ1.60-2.00 (m, 4H), 2.90 (dt, J=3.6 and 12.3 Hz, 0.5H), 3.00 (dd, J=4.2 and 13.3 Hz, 0.5H), 3.20-3.40 (2 m, 2H), 3.44-3.62 (m, 1.5H), 3.72 (bd, 0.5H), 4.32-4.60 (m, 3H), 4.83 (bs, 0.5H), 5.07 (bs, 0.5H), 7.07 (dd, J=3.2 and 9.4 Hz, 1H), 7.69 (m, 1H), 8.03 (d, J=9.1 Hz, 1H), 8.10 (s, 0.5H), 8.25 (s, 0.5H), 8.32 (dd, J=2.6 and 9.1 Hz, 1H), 8.56 (d, J=2.3 Hz, 1H).

A solution of 31 (0.025 g, 0.072 mmol) in THF (0.5 mL) was treated with $H_2SO_4$ (4 M, 0.25 mL) and heated at 60° C. for 1 hour, then the reaction was quenched by pouring onto ice. The mixture was brought to a basic pH with 4 M NaOH, and buffered to pH 10 with sat. $NaHCO_3$. The aqueous layer was extracted with $CH_2Cl_2$, the organic portions were combined, dried ($K_2CO_3$) and concentrated in vacuo to give 2-(2-(3-Fluoropropyl)piperazin-1-yl)-6-nitroquinoline, 1 as yellow oil (0.021 g, 90%). $^1H$ NMR ($CDCl_3$, 400 MHz) δ 1.56-2.10 (2 m, 5H), 2.91 (dt, J=3.3 and 12.3 Hz, 1H), 3.06 (dd, J=3.9 and 12.3 Hz, 1H), 3.14-3.38 (3 m, 3H), 4.40-4.60 (2 m, 2H, $CH_2F$), 4.81 (bs, 1H), 7.04 (d, J=9.4 Hz, 1H), 7.64 (d, J=9.1 Hz, 1H), 7.99 (d, J=9.4 Hz, 1H), 8.31 (dd, J=2.6 and 9.4 Hz, 1H), 8.54 (d, J=2.6 Hz, 1H).

Three examples of the radiolabelled forms of the invention ligands are described. These include carbon-11 and fluorine-18 radionuclide incorporations to afford the PET imaging tracers [$^{11}$C]13, [$^{18}$F]2S and [$^{18}$F]1.

The first example is the transformation of compound 24 (Scheme 2) to the radiolabelled MOM ligand [$^{11}$C]13 (Table 2) which is accomplished with the following protocol. Carbon-11 $CO_2$ was produced with a CTI RDS 111 cyclotron by the $^{14}N(p,\alpha)^{11}C$ reaction with 1% $O_2/N_2$ and subsequently trapped on carbospheres at room temperature using an established procedure [Jacobsen 1999]. The trap was heated to release the [$^{11}$C]$CO_2$ which was converted to [$^{11}$C]$CH_3$I by the established method of Langstrom [Mock 1995]. A solution of 24 (2 mg) in DMF (0.25 mL) was treated with sodium hydride (3 mg) at room temperature (3 mL borosilicate V-vial). The vial was sealed, cooled to −5° C., and the gaseous [$^{11}$C]$CH_3$I was passed through the solution. The mixture was heated for 2-3 min (100° C.) and then cooled to room temperature. The reaction was quenched with the addition of ethanol (0.15 mL), diluted with water (55 mL) and the crude 4'-amine-t-Boc ether intermediate (not shown) was isolated on a C-18 Sep-Pak cartridge. The cartridge was eluted with dichloromethane (2 mL). Dilution of the cartridge eluant with TFA:dicholoromethane (1:9) was followed by concentration of the solution in vacuo at 100° C. (5 min) to provide a crude residue of [$^{11}$C]13. Purification of the residue with reversed phase semi-preparative HPLC (Activon GoldPak, Excil ODS-B 10 μm, 250×10 mm; methanol:water:triethylamine, 1.86:1.0:0.0006) monitored with UV (254 nm) and radioactivity detection provided the pure (>95%) tracer [$^{11}$C]13. Routinely (n=4), [$^{11}$C]12 was afforded over a total time of 45-60 min, in a decay corrected, end of bombardment yield of 9-16%.

Another example of radiolabelling includes the formation of (S)-[$^{18}$F]MePrOF tracer [$^{18}$F]2S of the invention (Table 2). Radioactive fluoride ion was generated by irradiating oxygen-18 enriched water (>94%) in a silver coated target chamber with a 10 MeV proton beam of a CTI RDS-111 cyclotron. Following irradiation, the water (containing Ag[$^{18}$F]F, 175 μL) and dry acetonitrile (300 μL) were added to 2 μL of tetra-n-butyl-ammonium hydroxide (TBA-OH) in a siliconized vacutainer. The water was removed through azeotropic evaporation of the water/acetonitrile mixture at 100° C. (3 cycles) to afford [$^{18}$F]TBAF in >90% radiochemical yield. The [$^{18}$F]TBAF was then transferred to a reaction vial containing tosylate 27 (Scheme 2). The vial was sealed and heated at 100° C. for 10 min. The crude mixture was pushed through a silica gel cartridge with acetonitrile and evaporation of the solvent at 100° C. provided the crude labeled material in >50% decay corrected radiochemical yield. The crude material was treated with conc. $H_2SO_4$ for 10 min at 20° C. to remove the t-Boc protecting group. After diluting with 0.1 N NaOH, the solution was loaded onto a C-18 Sep-Pak cartridge and rinsed with water. The crude radiotracer (S)-[$^{18}$F]2 was eluted by flushing the cartridge with methanol. The methanol solution was diluted with water (1 mL) and the mixture was purified by semi-preparative HPLC (radioactivity detection). The product HPLC fraction was diluted with water and loaded onto a C-18 Sep-Pak cartridge and then eluted from the cartridge with ethanol. The purified tracer is routinely (n=9) obtained in a 15-30% decay corrected radiochemical yield in a completed radiochemical synthesis and purification time of approximately 90 minutes.

Another example of radiolabelling includes the formation of [$^{18}$F]PrOF tracer [$^{18}$F]1 of the invention (Table 2) employing radiofluorination conditions similar to those used for the formation of [$^{18}$F]2S. The [$^{18}$F$^-$]F$^-$ displacement of tosylate 30 utilizing [$^{18}$F]TBAF in acetonitrile at 100° C., followed by treatment of the crude radiolabelled material with 4 N $H_2SO_4$ at 100° C., aqueous NaOH and then a C-18 Sep-Pak cartridge with methanol elution afforded [$^{18}$F]1. Purification of [$^{18}$F]1 by semi-preparative HPLC (65:35:0.2 MeOH:H$_2$O:Et$_3$N) afforded pure [$^{18}$F]1 in a 8-11% end of bombardment, decay corrected radiochemical yield (n=3).

The compounds of the invention are potent (sub-nanomolar concentration) pharmacological inhibitor binding ligands of the serotonin transporter. Examples of the in vitro inhibition competitive pharmacological binding SERT potencies are shown in Table 3, where the binding constant K$_i$ values are reported as mean±s.e.m., n=3 or greater. The binding constants were determined using an established competition assay (rat frontal cortical SERT, rSERT; [$^3$H]Paroxetine, 3 h incubation time at 20° C., nonspecific binding determined as the difference in the absence and presence of saturating levels of non-radioactive 6-nitroquipazine) [Gerdes 2000] which is a modified method of Habert [Habert 1985]. The more potent enantiomeric stereochemical isomers are those with the (R)-configuration. The ligands of the invention are considered to have antidepressant qualities since they effectively compete with the radiolabelled form of the known antidepressant Paroxetine ([$^3$H]Paroxetine) at the serotonin transporter [Tatsumi 1997, Hyttel 1994].

TABLE 3

Examples of pharmacological binding of the 2'-alkyl-6-nitroquipazine analogs of the invention relative to the established lead agent 12.

| Cpd | R | Name | K$_i$ (nM)$^b$ | Reference |
|---|---|---|---|---|
| 12 | CH$_3$ (reference) | Me | 0.081 ± 61 | Gerdes 2000 |
| 13 | (±)-CH$_2$OCH$_3$ | MOM | 0.42 ± 0.01 | |
| 13R | (R)—CH$_2$OCH$_3$ | R-MOM | 0.25 ± 0.03 | |
| 13S | (S)—CH$_2$OCH$_3$ | S-MOM | 1.52 ± 0.10 | |
| 14 | (±)-CH$_2$OH | HOM | 0.68 ± 0.04 | |
| 2 | (±)-CH$_2$OCH$_2$CH$_2$CH$_2$F | MePrOF | 0.28 ± 0.09 | |
| 2R | (R)—CH$_2$OCH$_2$CH$_2$CH$_2$F | R-MePrOF | 0.25 ± 0.08 | |
| 2S | (S)—CH$_2$OCH$_2$CH$_2$CH$_2$F | S-MePrOF | 1.56 ± 0.88 | |

$^a$The symbol * indicates a stereochemical center, where (±) is the racemic forms, (R) is the R-configurational enantiomer and (S) is the S-configurational enantiomer.
$^b$Competitive binding, rat brain cortex homogenate, [$^3$H]paroxetine, 20° C., 3 h; n = 3.

In other pharmacological experiments, as shown in Table 4, the analogs of the invention were found to competitively inhibit tritiated serotonin ([$^3$H]5-HT) uptake into HEK-293 cells transfected with human serotonin transporter (hSERT) using an established procedure [Henry 2003, Henry 2006] that is carried out at 20° C. and for 3 h incubation time. The analog inhibition K$_i$ values occur with sub-nanomolar concentrations, where it is found that the (R)-configurational stereoisomers are with greater potency than the opposing (S)-enantiomeric forms. The ligands of the invention are considered to have antidepressant qualities since they effectively inhibit the uptake of the radiolabelled form of the neurotransmitter 5-HT by the human serotonin transporter [Hyttel 1994].

TABLE 4

Examples of pharmacological inhibition of 5-HT uptake by analogs of this invention.

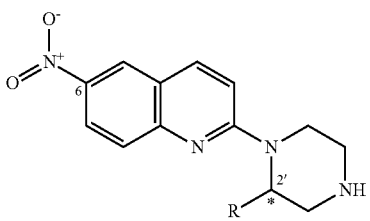

| Cpd | R | Name | K$_i$ (nM)$^b$ |
|---|---|---|---|
| 13 | (±)-CH$_2$OCH$_3$ | MOM | 0.47 |
| 13R | (R)—CH$_2$OCH$_3$ | R-MOM | 0.15 |
| 13S | (S)—CH$_2$OCH$_3$ | S-MOM | 1.66 |

$^a$The symbol * indicates a stereochemical center, where (±) is the racemic forms, (R) is the R-enantiomer and (S) is the S-enantiomer.
$^b$Competitive binding, hSERT HEK-293 cells, [$^3$H]5-HT, 20° C., 3 h.

Example 1

In Vivo Tracer Studies in Rats

Figure 2:
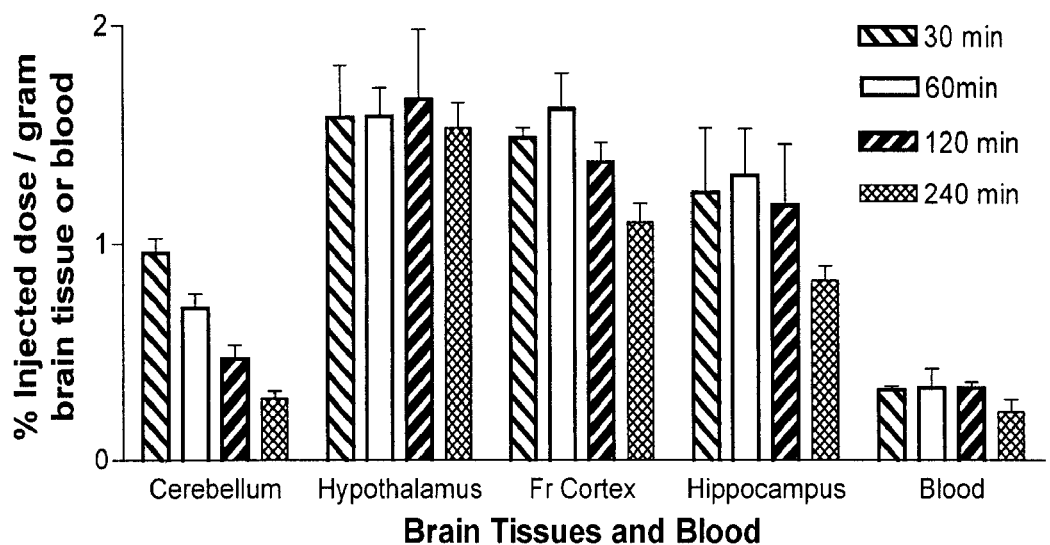
FIG. 2 shows regional rat brain uptake (% ID/g) of tracer [$^{18}$F]]2 decay corrected radioactivity in dissected brain regions at various times; n=3.
Figure 3:
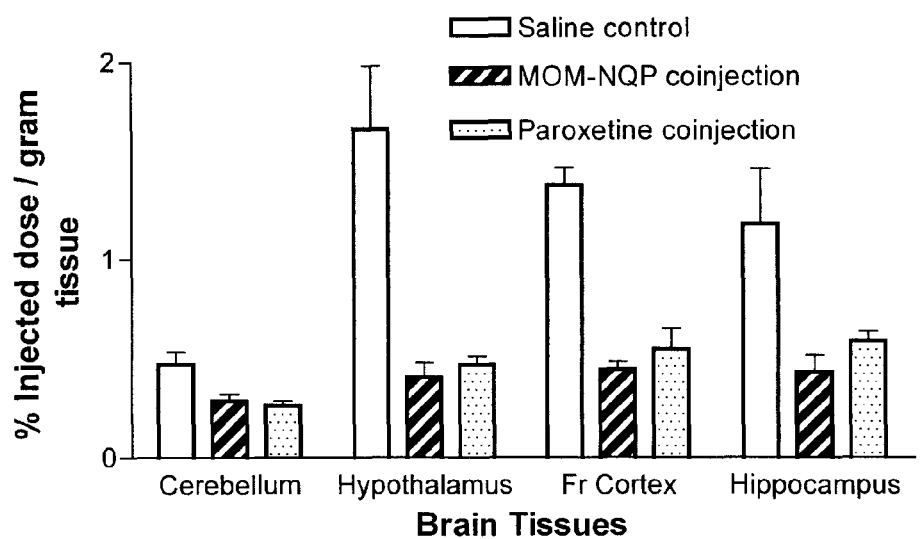
FIG. 3 shows regional rat brain tracer uptake of [$^{18}$F]]2 at 120 min post tracer injection in control (untreated, saline) rats, and with rats co-injected with tracer plus SERT inhibitors Paroxetine or the MOM ligand 13 (co-injection does of 2.5 mg/kg); n=3.
Figure 4:
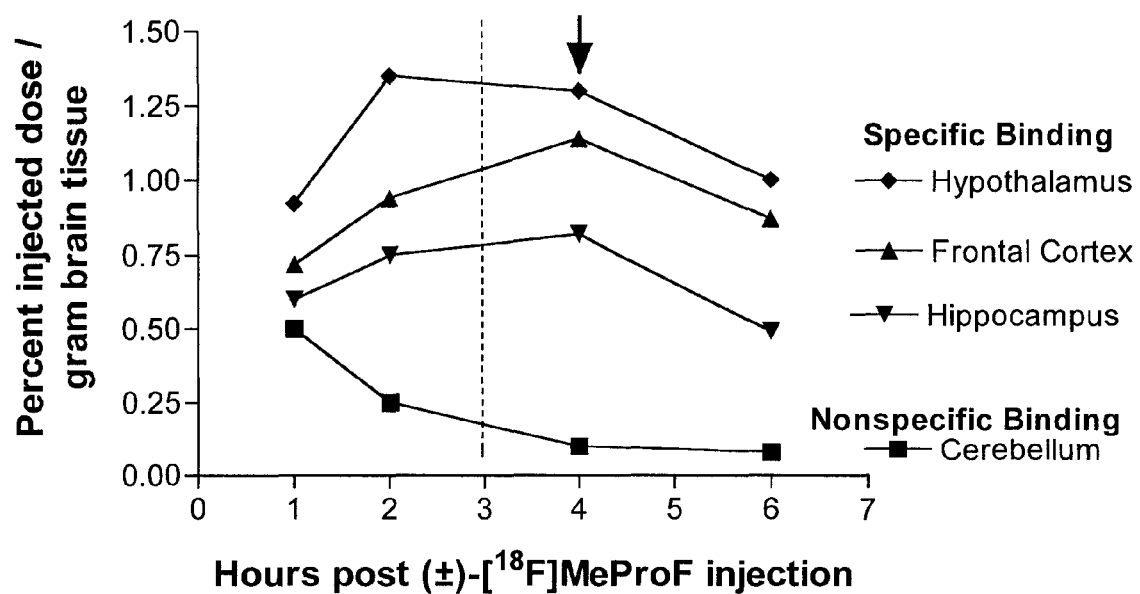
FIG. 4 shows regional rat brain SERT binding of tracer [$^{18}$F]]2 at 1-6 h post tracer injection, delineating specific binding within the SERT rich hypothalamus, moderate SERT density regions (hippocampus and frontal cortex) and non-specific binding within cerebellum. Specific binding was defined as the difference between total binding radioactiviy and binding radioactivity in the presecenfo SERT antidepressant inhibitor Paroxetine (co-injection dose at 2.5 mg/Kg). For all points (n=3) error bars have been omitted for graphical clarity. The arrow (4 h) is a time period of low cerebellum activity and high specific binding within rat cerebral activity and high specific binding within rat cerebral regions of interest. The dashed line is the time (3 h) during the rat study that correlates to a monkey PET scan sampling (3 h) performed with tracer [$^{18}$F]]2, as detailed in FIG. 5.
Figure 5A:
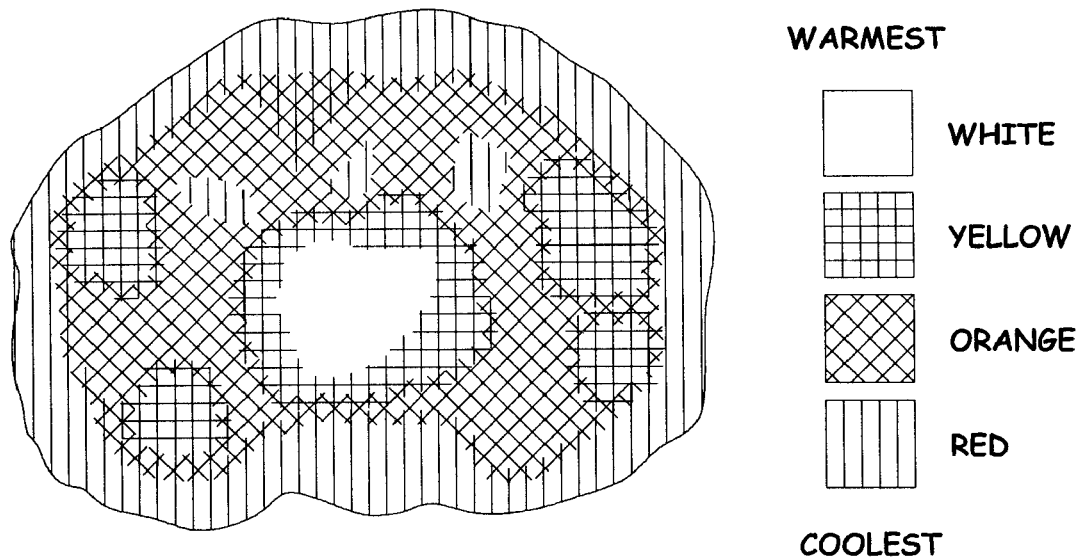
FIG. 5 shows cerebral PET images of the accumulation of tracer [$^{18}$F] 2 in *macaca mulatta* monkey coronal sections acquired at 3 h post tracer injection, depicted in heat scale format.
Figure 5B:
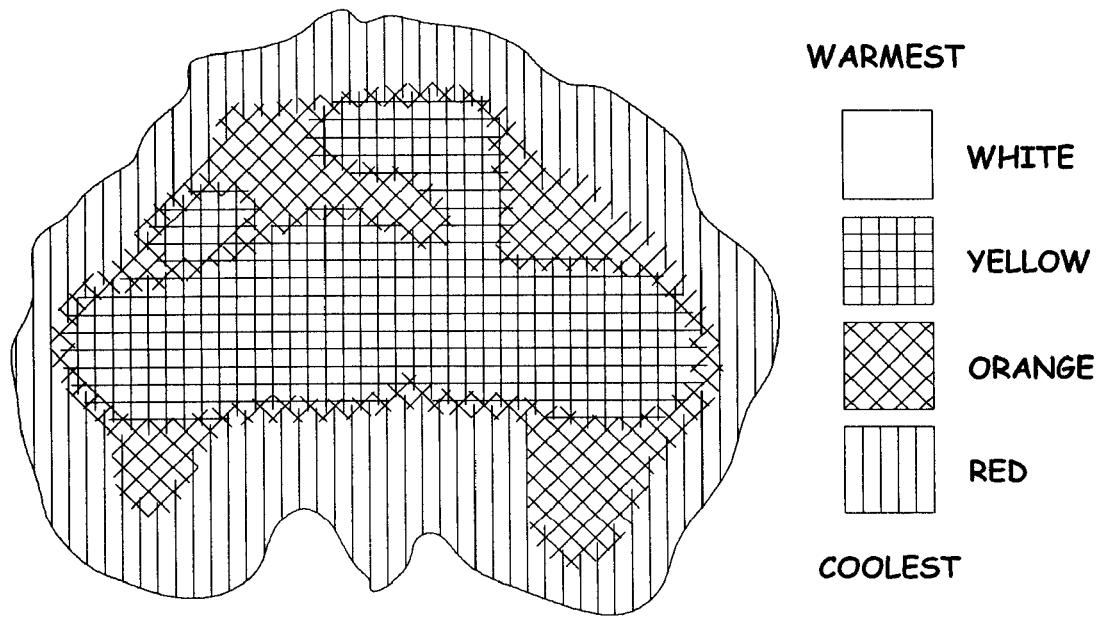

Examples of the biodistributions of the invention include studies with tracer [$^{18}$F]2 in rats as shown in FIGS. 1-4, which are considered representative of in vivo performance as an imaging agent for SERT [Huang 2005, Biegon 1993]. The biodistribution protocols followed established sacrifice, dissect and count methods [Biegon 1993] under several conditions, utilizing male Sprague-Dawley rats, lateral tail vein injection of tracer with three rat subjects per group and where average decay corrected percent injected dose activity values per gram tissue (% ID/g)±s.e.m. error bars are shown. FIG. 1 demonstrates a significant percentage of the injected tracer dose penetrates the brain (>1%), relative to the other tissues examined. FIG. 2 further delineates a high partition of the tracer into various brain regions, where the hypothalamus, frontal cortex and hippocampus regions are associated with the cerebral limbic system and are found to be with moderate SERT protein densities whereas the cerebellum is with low SERT protein density and considered a reference region. The later 240 minute time points of FIG. 2 describe favorable respective relative ratios of tracer activity within tissues, including hypothalamus, frontal cortex or hippocampus vs. the low SERT density cerebellum region. FIG. 3 delineates the blocking experiments of tracer [$^{18}$F]2 in various cerebral tissues at 120 minutes post tracer injection, in the absence and presence (co-injection with tracer at 2.5 mg/Kg) of the non-radioactive potent antidepressant Paroxetine or ligand 13, thereby delineating that the tracer is specifically bound to the SERT protein within the cerebral regions. FIG. 4 demonstrates the SERT specific binding of the tracer in different cerebral regions over time, where specific activity is defined as the radioactivity difference between the absence and presence of non-radioactive antidepressant Paroxetine [Biegon 1993, Jagust 1993, Jagust 1995]. The FIG. 4 later time points of 4 and 6 h delineate that the specific tracer binding tissue ratios of hypothalamus, frontal cortex or hippocampus vs. cerebellum are high, thus demonstrating efficacy of the tracer for quantitative determinations of SERT densities in cerebral regions of interest useful for PET imaging of SERT in live brain [Huang 2005, 2004, 2002].

Example 2

Monkey PET Scan with Tracer [$^{18}$F]2

To associate tracer [$^{18}$F]2 brain penetration and regional cerebral localization of in rat (e.g., Graph 4) to non-human primate brain and cerebral regions of interest with various known SERT densities, monkey (*macaca mulatta*) PET scans were performed. A portion of the results obtain are shown in FIG. 2. In brief, the monkey was anesthetized (ketamine, 15 mg/Kg, i.m. injection), intubated and placed on isoflurane anesthesia and then kept normothermic (heating blanket), hydrated (saphenous catheter), and pO$_2$ was monitored with an oximeter. The subject was placed in a stereotaxic frame, positioned in a Siemens-CTI ECAT EXACT HR 47-slice PET imaging scanner in two-dimensional (2D) acquisition mode. Monkey cerebral slice images were acquired in the coronal plane, after a 20 min transmission scan was obtained (using a rotating $^{68}$Ge source consisting of 3 rods of 2 mCi/rod) to correct for photon attenuation. Emission data were collected according to the 3 h protocol that began simultaneously with the injection of tracer [$^{18}$F]2 (i.v., 5 mCi; specific activity 3200 mCi/µmol). Coronal PET images were sampled over 0-3 h for the accumulation of [$^{18}$F]2 providing the opportunity to compare activity found within regions of interest (ROIs) vs. the cerebellum reference region using the method of Logan [Logan 1990]. Cerebral 2D ROIs were drawn for multiple ROIs (brain stem, thalamus, hypothalamus, hippocampus, putamen, frontal cortex, cerebellum, among others) with reference to a previously acquired monkey MRI scan that together were correlated to an established monkey brain atlas. Representative coronal slice data sampled at 3 h are depicted in FIG. 2 (heat scale format), shown as panel A (SERT rich and moderate density, thalamus and hypothalamus, respectively) and panel B (SERT low-moderate density region, frontal cortex). The comparative analysis of *macaca mulatta* PET scan data over time, per cerebral regions of interest relative to the cerebellum reference region, reveal high cerebral ROI:cerebellum ratios that correlate to the rat SERT specific tracer binding ratios established in FIG. 4.

It is understood that the foregoing examples are merely illustrative of the present invention. Certain modifications of the compounds and/or methods employed may be made and still achieve the objectives of the invention. Such modifications are contemplated as within the scope of the claimed invention.

REFERENCES

Bedurftig S, Wunsch B (2004) Chiral, nonracemic (piperazin-2-yl)methanol derivatives with [sigma-receptor affinity. Bioorg Med Chem 12:3299-3311.

Bedurftig S, Wunsch B (2006) Synthesis and receptor binding studies of 3-substituted piperazine derivatives. Eur J Med Chem 41:387-396.

Biegon A, Mathis C A, Hanrahan S M, Jagust W J (1993) [$^{125}$I]5-Iodo-6-nitroquipazine: a potent and selective ligand for the 5-hydroxytryptamine uptake complex. II. In vivo studies in rats. Brain Res 619:236-46.

Bishop J E, Mathis C A, Gerdes J M, Whitney J M, Eaton A M, Mailman R B (1991) Synthesis and in vitro evaluation of 2,3-dimethoxy-5-(fluoroalkyl)-substituted benzamides: high affinity ligands for CNS dopamine D$_2$ receptors. J Med Chem 34:1612-1624.

Elfving B, Bjornholm B, Ebert B, Knudsen G M. (2001) Binding characteristics of selective serotonin reuptake inhibitors with relation to emission tomography studies. Synapse 41:203-11.

Frankle G W, Huang Y, Hwang D-R, Talbot P S, Slifstein M, Van Heertum, R, Abi-Dargham A, Laruelle M (2004) Comparative evaluation of serotonin transporter radioligands $^{11}$C-DASB and $^{11}$C-McN 5652 in healthy humans. J Nuc Med 45:682-694.

Gerdes J M, DeFina S C, Wilson P A, Taylor S E (2000) Serotonin transporter inhibitors: synthesis and binding potency of 2'-methyl- and 3'-methyl-6-nitroquipazine. Bioorg Med Chem Lett 10:2643-2646.

Habert E, Graham D, Tahraoui L, Claustre Y, Langer S Z (1985) Characterization of [$^3$H]paroxetine binding to rat cortical membranes. Eur J Pharmacol 118:107-114.

Henry K L, Adkins E M, Han Q, Blakely R D (2003) Serotonin and cocaine-sensitive inactivation of human serotonin transporters by methanethiosulfonates targeted to transmembrane domain I. J. Biol. Chem. 278:37052-37063.

Henry L K, Field J R, Adkins E M, Parnas M L, Vaughan R A, Zou M-F, Newman A H, Blakely R D (2006) Tyr-95 and Ile-172 in transmembrane segments 1 and 3 of the human serotonin transporters interact to establish high affinity recognition of antidepressants. J. Biol. Chem. 281:2012-2023.

Hesse S, Barthel H, Schwarz J, Sabri O, Muller U (2004) Advances in in vivo imaging of serotonergic neurons in neuropsychiatric disorders. Neurosci Biobehavioral Rev 28:547-563.

Huang Y, Bae S-A, Zhu Z, Gui N, Roth B L, Laruelle M (2005) Fluorinated diaryl sulfides as serotonin transporter ligands: synthesis, structure-activity relationship study, and in vivo evaluation of fluorine-18-labeled compounds as PET imaging agents. J Med Chem 48:2559-2570.

Huang Y, Hwang D-R, Bae S-A, Sudo Y, Guo N, Zhu Z, Narendran R, Laruelle M (2004) A new positron emission tomography imaging agents for the serotonin transporter: synthesis, pharmacological characterization and kinetic analysis of [$^{11}$C]2-[2-(dimethylaminomethyl)phenylthio-5-fluoromethylphenylamine ([$^{11}$C]AFM). Nuc Med Biol 31:543-556.

Huang Y, Hwang D R, Narendran R, Sudo Y, Chatterjee R, Bae S A, Mawlawi O, Kegeles L S, Wilson A A, Kung H F, Laruelle M. (2002) Comparative evaluation in nonhuman primates of five PET radiotracers for imaging the serotonin transporters: [$^{11}$C]McN 5652, [$^{11}$C]ADAM, [$^{11}$C]DASB, [$^{11}$C]DAPA, and [$^{11}$C]AFM. J Cereb Blood Flow Metab 22:1377-98.

Hyttel J (1994) Pharmacological characterization of selective serotonin reuptake inhibitors (SSRIs). Int. Clinical Psychopharmacol (9 Suppl) 1:19-26.

Jacobsen E J, Stelzer L S, TenBrink R F, Belonga K L, Carter D B, Im H K, Im W B, Sethy V H, Tang A H, VonVoigtlander P F, Petke J D, Zhong W-Z, Mickelson J W (1999) J Med Chem 42:1123.

Jagust W J, Eberling J L, Roberts J A, Brennan K M, Hanrahan S M, VanBrocklin H, Enas J D, Biegon A, Mathis C A (1993) In vivo imaging of the 5-hydroxytryptamine reuptake site in primate brain using single photon emission computed tomography and [$^{123}$I]5-iodo-6-nitroquipazine. Eur J Pharmacol 242:189-93.

Jagust W J, Eberling E L, Biegon A, Taylor S E, VanBrocklin H F, Jordan S, Hanrahan S M, Roberts J A, Brennan K M, Mathis C A (1995) Iodine-123-5-iodo-6-nitroquipazine: SPECT radiotracer to image the serotonin transporter. J Nuc Med 37:1207-14.

Karramkam M, Dolle F, Valette H, Besret L, Bramoulle Y, Hinnen F, Vaufrey F, Franklin C, Bourg S, Coulon C, Ottaviani M, Delaforge M, Loc'h C, Bottlaender M, Crouzel C. (2002) Synthesis of a fluorine-18-labelled derivative of 6-nitroquipazine, as a radioligand for the in vivo serotonin transporter imaging with PET. Bioorg Med Chem 10:2611-23.

Lee B S, Chu S, Lee K C, Lee B-S, Chi D Y, Choe Y S, Kim S E, Song Y S, Jin C (2003) Synthesis and binding affinities of 6-nitroquipazine analogs for serotonin transporter: Part 3. A potential 5-HT transporter imaging agent, 3-(3-[$^{18}$F]fluorpropyl)-6-nitroquipazine. Biorg Med Chem 11:1-10.

Lee B S, Lee K C, Chu S Y, Choy Y S, Kim B-T, Chi D Y (1999) A potential 5-HT transporter imaging agent: 3-(3-[$^{18}$F]fluoropropyl)-6-nitroquipazine. J Label Compd Radio-pharm 42 (suppl 1):54.

Logan J, Fowler J, Volkow N D, et al. (1990) Graphical analysis of reversible radioligands binding from time-activity measurements applied to [N-$^{11}$Cmethyl]-(–)-cocaine PET studies in human subjects. J Cereb Blood Flow Metab 10:740-747.

Lundkvist C, Loch C, Halldin C, Bottlaender M, Ottaviani M, Coulon C, Fuseau C, Mathis C, Farde L, Maziere B. (1999) Characterization of bromine-76-labelled 5-bromo-6-nitroquipazine for PET studies of the serotonin transporter Nucl Med Biol 26:501-7.

Mock B H, Vavrek M T, Mulholland G K (1995) Solid-phase reversible trap for [$^{11}$C]carbon dioxide using carbon molecular sieves. Nucl Med Biol 22:667-670.

Naylor A, Judd D B, Lloyd J E, Scopes D I C, Hayes A G, Birch P J (1993) A potent new class of k-receptor agonists: 4-substituted 1-(arylacetyl)-2-[(dialkylamino)methyl]piperazines. Med Chem 36:2075-2083.

Sandell J, Halldin C, Sovago J, Chou Y—H, Gulyás B, Yu M, Emond P, Någren K, Guilloteau D, Farde L (2002) PET examination of [$^{11}$C]5-methyl-6-nitroquipazine, a radioligand for visualization of the serotonin transporter. Nuc Med Biol 29:651-656.

Tatsumi M, Groshan K, Blakely R D, Richelson E (1997) Pharmacological profile of antidepressants and related compounds at human monoamine transporters. Eur J Pharmacol 340:249-258.

The invention claimed is:

1. A compound having the following structure:

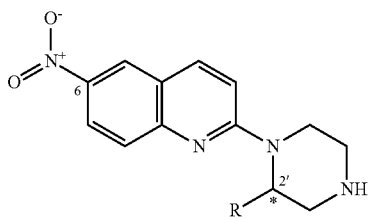

wherein R is selected from the group consisting of CH$_2$OCH$_3$, CH$_2$OH, CH$_2$CH$_2$CH$_2$OCH$_3$, CH$_2$CH$_2$CH$_2$OH, CH$_2$CH$_2$CH$_2$F and CH$_2$OCH$_2$CH$_2$CH$_2$F and enantiomers thereof.

2. The compound of claim 1, wherein R is CH$_2$OCH$_3$.
3. The compound of claim 1, wherein R is CH$_2$OH.
4. The compound of claim 1, wherein R is CH$_2$CH$_2$CH$_2$OCH$_3$.
5. The compound of claim 1, wherein R is CH$_2$CH$_2$CH$_2$OH.
6. The compound of claim 1, wherein R is CH$_2$CH$_2$CH$_2$F.
7. The compound of claim 1, wherein R is CH$_2$OCH$_2$CH$_2$CH$_2$F.

8. A pharmaceutical composition comprising a compound having the following structure:

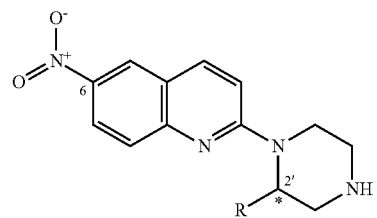

wherein R is selected from the group consisting of CH$_2$OCH$_3$, CH$_2$OH, CH$_2$CH$_2$CH$_2$OCH$_3$, CH$_2$CH$_2$CH$_2$OH, CH$_2$CH$_2$CH$_2$F and CH$_2$OCH$_2$CH$_2$CH$_2$F and enantiomers thereof; and
a pharmaceutically acceptable carrier.

9. A method of treating depression comprising administering a therapeutically effective amount of a compound having the following structure:

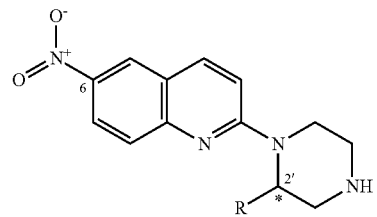

wherein R is selected from the group consisting of CH$_2$OCH$_3$, CH$_2$OH, CH$_2$CH$_2$CH$_2$OCH$_3$, CH$_2$CH$_2$CH$_2$OH, CH$_2$CH$_2$CH$_2$F and CH$_2$OCH$_2$CH$_2$CH$_2$F and enantiomers thereof.

10. The method of claim 9, wherein R is CH$_2$OCH$_3$.
11. The method of claim 9, wherein R is CH$_2$OH.
12. The method of claim 9, wherein R is CH$_2$CH$_2$CH$_2$OCH$_3$.
13. The method of claim 9, wherein R is CH$_2$CH$_2$CH$_2$OH.
14. The method of claim 9, wherein R is CH$_2$CH$_2$CH$_2$F.
15. The method of claim 9, wherein R is CH$_2$OCH$_2$CH$_2$CH$_2$F.

* * * * *